(12) United States Patent
Nishio et al.

(10) Patent No.: US 8,470,549 B2
(45) Date of Patent: Jun. 25, 2013

(54) METHOD FOR DETECTING AN ANTIGEN

(75) Inventors: Kazuaki Nishio, Osaka (JP); Nozomu Matsukawa, Nara (JP); Shigeo Yoshii, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/536,202

(22) Filed: Jun. 28, 2012

(65) Prior Publication Data

US 2012/0309033 A1 Dec. 6, 2012

Related U.S. Application Data

(63) Continuation of application No. PCT/JP2011/007240, filed on Dec. 22, 2011.

(30) Foreign Application Priority Data

Jun. 6, 2011 (JP) .................................. 2011-125972

(51) Int. Cl.
*G01N 21/78* (2006.01)
*G01N 33/53* (2006.01)
*G01N 33/52* (2006.01)

(52) U.S. Cl.
USPC .......................................... 435/7.92; 435/7.1

(58) Field of Classification Search
None
See application file for complete search history.

(56) References Cited

U.S. PATENT DOCUMENTS

| 2005/0282237 A1 | 12/2005 | Ishimori |
| 2010/0040910 A1 | 2/2010 | Kajino et al. |

FOREIGN PATENT DOCUMENTS

| EP | 2063264 | * | 5/2009 |
| JP | 2005-351662 | | 12/2005 |
| WO | WO 2008/029843 A1 | | 3/2008 |
| WO | WO 2011/151964 A1 | | 12/2011 |

OTHER PUBLICATIONS

Shin et al., (Archives of Biochemistry and Biophysics; 2000, 384 vol. 109-115).*
Roberts et al., (Journal of Biological Chemistry, vol. 278, No. 34, Issue of Aug. 22, pp. 31958-31963).*
I. Pozdnyakova et al., "Non-linear effects of macromolecular crowding on enzymatic activity of multi-copper oxidase," Biochimica et Biophysica Acta, Mar. 2, 2010, vol. 1804/No. 4, pp. 740-744.
International Search Report issued in International Patent Application No. PCT/JP2011/007240 dated Jan. 31, 2012.

* cited by examiner

*Primary Examiner* — Peter J Reddig
*Assistant Examiner* — Carmencita M Belei
(74) *Attorney, Agent, or Firm* — McDermott Will & Emery LLP

(57) ABSTRACT

The present invention relates to a method for detecting an antigen with use of an antibody and an enzyme. Specifically, the present invention provides a method for detecting an antigen without use of a labeled-antibody. the method comprises immersing particles in a first buffer solution which is predicted to contain the antigen; wherein an antibody and a multi-copper oxidase CueO are immobilized on each surface of the particles, and the antibody reacts specifically with the antigen. The method further comprises the following steps recovering the obtained particles; mixing the particles recovered, an oxidation-reduction indicator (reductant), and a second buffer solution so as to prepare a reaction solution; measuring an activity degree of the multi-copper oxidase CueO contained in the reaction solution; determining that the first buffer solution contains the antigen based on the above activity degree.

5 Claims, 3 Drawing Sheets

METHOD FOR DETECTING AN ANTIGEN

RELATED APPLICATIONS

This is a continuation of International Application No. PCT/JP2011/007240, with an international filing date of Dec. 22, 2011, which claims priority of Japanese Patent Application No. 2011-125972, filed on Jun. 6, 2011, the contents of which are hereby incorporated by reference.

TECHNICAL FIELD

The present invention relates to a method for detecting an antigen with use of an antibody and an enzyme.

BACKGROUND ART

Japanese Patent Publication No. 4271086 (hereafter, Patent Literature 1; this literature corresponds to US Pre-Grant Patent Application Publication No. 2005/0282237) discloses an enzyme immunoassay method. FIG. 2 shows a sandwich method, which is included in the enzyme immunoassay method.

As shown in FIG. 2, a support 107 has an antibody 108 on its surface. The sample containing an antigen 109 is supplied to the surface of the support 107 to cause the antigen 109 to be bound specifically to the antibody 108. Subsequently, the sample containing the unreacted antigen 109 was removed from the support by washing.

Next, a labeled-antibody 111 comprising an enzyme 110 which detects the antigen 109 is supplied to the surface of the support 107 to form the complex composed of the antibody 108, the antigen 109, and the labeled-antibody 111. Subsequently, the sample containing the unreacted labeled-antibody 111 was removed by washing.

Finally, a substrate 112 of the enzyme 110 is supplied to the surface of the support 107. The enzyme 110 reacts with the substrate 112 metabolically to form a product 113. The luminescence degree or light absorption degree of the product 113 is measured so as to detect the antigen 109 indirectly.

CITATION LIST

Patent Literature

[Patent Literature 1] Japanese Patent Publication No. 4271086.

SUMMARY OF INVENTION

Technical Problem

However, the sandwich method requires not only the antigen 108 but also the labeled-antibody 111 comprising the enzyme 110. It is necessary that the labeled-antibody 111 is supplied after the specific reaction generated between the antibody 108 and the antigen 109. Furthermore, the unreacted labeled-antibody 111 is required to be removed.

One of the purposes of the present invention is to provide a method for detecting an antigen without use of a labeled-antibody.

Solution to Problem

The present invention is directed to a method for detecting an antigen, the method comprises steps of:

(a) immersing particles in a first buffer solution which is predicted to contain the antigen; wherein
an antibody and a multi-copper oxidase CueO are immobilized on each surface of the particles, and
the antibody reacts specifically with the antigen;
(b) recovering the particles obtained in the step (a);
(c) mixing the particles recovered in the step (b), an oxidation-reduction indicator (reductant), and a second buffer solution so as to prepare a reaction solution; wherein
the second buffer solution contains a substrate of the multi-copper oxidase CueO; and
the second buffer solution has an ion strength falling within the range of not less than 0.3 mM and not more than 1.0 mM;
(d) measuring an activity degree of the multi-copper oxidase CueO contained in the reaction solution obtained in the step (c) by an absorbance measurement technique; and
(e) determining that the first buffer solution contains the antigen if the following formula is satisfied:

the activity degree measured in the step($d$)≧1.4× (blank value)

wherein the blank value represents the activity degree of the multi-copper oxidase CueO measured by an absorbance measurement technique in which the antigen is not used, however, the particles and the second buffer solution are used.

Advantageous Effects of Invention

In an aspect, the present invention provides a method for detecting an antigen without use of a labeled-antibody.

DESCRIPTION OF EMBODIMENTS

Figure 1:
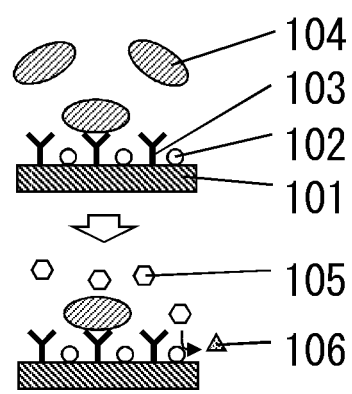
FIG. 1 shows a reaction flowchart of the method for detecting an antigen according to the present invention.
Figure 2:
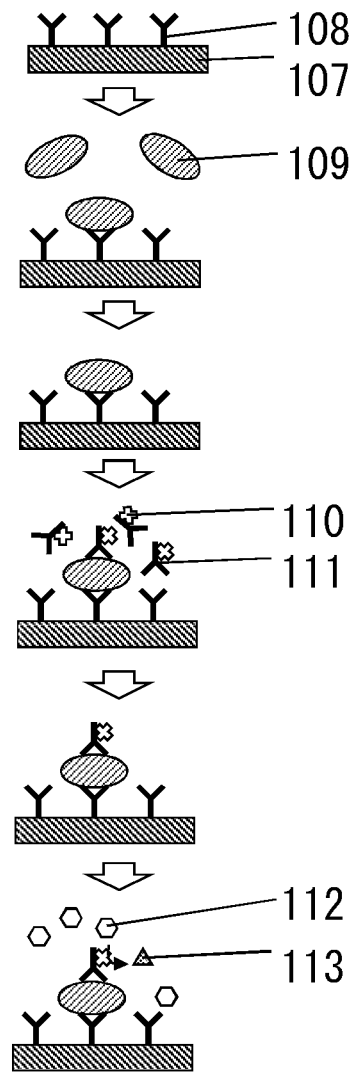
FIG. 2 shows a reaction flowchart of the conventional enzyme immunoassay method (Sandwich method).
Figure 3:
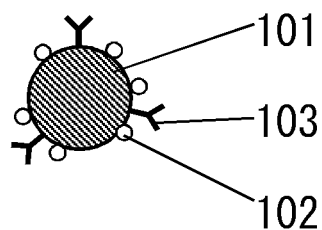
FIG. 3 shows an example of a particle support where a CueO and an antibody are immobilized.

An illustrative embodiment of the present invention is described below with reference to the drawings.
FIG. 1 shows a reaction flowchart of the method for detecting an antigen according to the present invention.
(Step (a))
In the step (a), particles 101 are immersed in a first buffer solution which is predicted to contain an antigen 104.
As shown in FIG. 3, each particle 101 comprises a multi-copper oxidase 102 and an antibody 103 on its surface. Hereinafter, the multi-copper oxidase 102 is referred to as "CueO".
In light of increasing amounts of the immobilized antibody 103 and CueO 102, it is preferable that each particle 101 is made of a particle having a diameter of 10-20 nanometers.
As shown in FIGS. 1 and 3, the antibody 103 and CueO 102 are immobilized on the surface of the particles 101. The antibody 103 reacts specifically with the antigen 104.
In light of easily immobilizing the antibody 103 and the CueO 102, an example of the material of the particles 101 is noble metal. An example of the noble metal is gold, silver, or platinum. Gold is preferred.
The antibody 103 may be a polyclonal antibody or a monoclonal antibody. A Fab fragment or a F(ab')2 fragment of an antibody may be used as the antibody 103, which is created through artificially removing its Fc or a portion thereof from the antibody.

The CueO 102 is one enzyme which catalyzes an oxidation-reduction reaction. As shown in FIG. 1, the CueO 102 performs four-electron reduction of the substrate 105 composed of oxygen molecule and catalyzes the reaction in which water is generated as a product 106. The active center of the CueO 102 is composed of four copper ions each having differential property called type 1, type 2, type 3a, and type 3b.

It is preferred that the CueO derived from *Escherichia coli* is used.

The method for immobilizing the antibody 103 and the multi-copper oxidase 102 on the particles 101 includes the following method (a):

Method (a): a method using non-specific adsorption due to hydrophobic interaction generated between the antibody 103 and the multi-copper oxidase 102.

An example of the antigen 104 detected by the present invention is a virus, a *bacillus*, a fungus, a protein, or an oligonucleotide. A virus, a *bacillus*, or a fungus is preferred.

An example of the first buffer solution is a Tris-buffered HCl solution, a Tris-buffered saline, or a phosphate buffer saline. Preferably, the first buffer solution has a near-neutral pH.

The immersion causes the specific binding of the antibody 103 to the antigen 104. Subsequently, the first buffer solution containing the unreacted antigen 104 was removed from the surface of the particles 101.

In the present invention, the specific binding of the antibody 103 to the antigen 104 increases the enzyme activity of the CueO 102.

(Step (b))

In the step (b), the particles 101 obtained in the step (a) are recovered. More particularly, the particles 101 can be recovered by centrifugation. A filter may be used to recover the particles 101.

(Step (c))

In the step (c), the particles 101 recovered in the step (b), an oxidation-reduction indicator (reductant), and a second buffer solution are mixed to prepare a reaction solution. The second buffer solution may contain the oxidation-reduction indicator (reductant) beforehand, prior to the addition of the particles 101 to the second buffer solution. Instead of this, the oxidation-reduction indicator (reductant) may be added to the second buffer solution, after the particles 101 are added to the second buffer solution.

The second buffer solution contains a substrate 105 of the CueO 102. An example of the substrate 105 is oxygen or proton. Oxygen and proton are contained in an ordinal and commercially-available buffer solution.

An example of the oxidation-reduction indicator is 2,2'-Azinobis(3-ethylbenzothiazoline-6-sulfonic Acid (hereinafter, referred to as "ABTS"), p-Phenylenediamine, or 2,6-Dimethoxyphenol. ABTS is preferred, since ABST (reductant) is commercially-available and easy to be acquired.

It is preferred that the second buffer solution has pH of not less than 4.5 and not more than 5.5. Sodium hydroxide, potassium hydroxide, ammonia, or trimethylammonium are used to adjust the pH of the second buffer solution. An example of the second buffer solution is an acetic acid buffer solution, a citrate buffer solution, a succinic acid buffer solution, a phthalic acid buffer solution, or 2-morpholinoethanesulfonic acid buffer solution, which is referred to as "MES". An acetic acid buffer solution is preferred.

The second buffer solution is required to have an ionic strength falling within a range of not less than 0.3 mM and not more than 1.0 mM. When the ionic strength is less than 0.3 mM, it is difficult to ensure the stability of the pH. When the ionic strength is more than 1.0 mM, as is clear from the examples described later, it is difficult to detect the antibody contained in the first buffer solution.

(Step (d))

In the step (d), the activity degree of the CueO contained in the reaction solution obtained in the step (c) is measured by an absorbance measurement technique.

It is preferred that a visible-ultraviolet spectrophotometer is used to measure the absorbance.

A specific procedure for measuring the absorbance is described below. First, after the particles 101 are immersed in the second buffer solution in the step (c), the absorbance is measured continuously for a predetermined period, and a change amount of the absorbance per unit time is recorded. The oxidation-reduction indicator (reductant) contained in the reaction solution is oxidized by the CueO. Since the absorbance of the oxidation-reduction indicator in the oxidation state is different from the absorbance of the oxidation-reduction indicator in the reduction state, the change amount of the oxidation-reduction indicator is calculated from the absorbance.

The activity degree of CueO is calculated from the change amount of the oxidation-reduction indicator oxidized per unit time and the amount of the CueO used in the measurement.

(Step (e))

In the step (e), it is determined that the first buffer solution contains the antibody, if the following formula is satisfied.

$$\text{(the activity degree of the CueO measured in the step (d))} \geq 1.4 \times \text{(blank value)}$$

Here, the blank value is the activity degree of the CueO measured by the absorbance measurement technique where the antigen is not used, however, the particles 101 and the second buffer solution are used.

The blank value may be calculated in parallel with the step (c). Alternatively, the blank value is calculated beforehand.

The present invention is described in more detail by the following example 1.

(Preparation of a CueO Solution)

As described below, a CueO derived from *Escherichia coli* (K-12) was produced in the *Escherichia coli* as a recombinant CueO, and the CueO was purified.

The gene of the CueO was amplified by a PCR method using *Escherichia coli* genomic DNA (LA genome DNA set for PCR, available from Takara Bio Inc.).

In the PCR, a base sequence coding for a histidine tag was added to an oligo DNA primer, and the histidine tags were added to the carboxyl terminal side of the amino acid sequence of the CueO.

The amplified DNA fragment was cloned (In-Fusion Dry-Down PCR Cloning Kits; available from Clontech laboratories, Inc.) to an expression vector (pRSFDuet-1, available from Merck KGaA). With use of the expression vector, *Escherichia coli* (BL21(DE3); available from Agilent Technologies, Inc.) was transformed. The transformed *Escherichia coli* were incubated for sixteen hours on a LB broth containing copper sulfate with a concentration of 1 mM.

A periplasm fraction was extracted from the recovered fungus body, and CueO was purified from the extraction liquid with use of a histidine tag purification column (TALON CellThru Resin; available from Clontech laboratories, Inc.) and an anion-exchange column (HiTrap Q HP 5 mL; available from GE Healthcare).

With use of a desalination column (HiTrap desalting; available from GE Healthcare), the solvent of the solution containing the purified CueO was substituted with 10 mM of tris-hydrochloric acid buffer solution (pH: 7.5). Subsequently, the CueO solution was condensed with use of the ultrafiltration unit (Amicon Ultra-4, MWCO: 30,000; available from Millipore Corp.). The condensed CueO solution has a concentration of 1 mg/mL. The concentration of the CueO solution was measured by the Bradford method using Bovine Serum Albumin (BSA) as a standard. The obtained CueO solution was stored at four degrees Celsius.

(Preparation of the Antibody)

An anti-Bovine Serum Albumin antibody (anti-BSA antibody [Rabbit], 1 mg/mL, available from Bethyl Laboratories, Inc.) was used as antibody 103. The antibody was stored at a temperature of 4 degrees Celsius.

(Immobilization of the CueO 102 and the Antibody 103 to the Particles 101)

A dispersion liquid of gold particles each having a diameter of 20 nanometers (Gold Colloid 20 nml; BBI Holdings Plc) was used. The gold particles served as the particles 101. The dispersion liquid (12 milliliters) and the antibody (0.12 milliliters) were mixed and left alone for 40 minutes at a temperature of 23 degrees Celsius. Subsequently, the CueO solution (0.12 milliliters) was added and left alone for 40 minutes at a temperature of 23 degrees Celsius. Furthermore, a 10% aqueous solution (0.12 milliliters) of polyoxyethylene(20) sorbitan monolaurate (available from Affymetrix, Inc) was added and left alone for 40 minutes at a temperature of 23 degrees Celsius.

Next, the CueO and the antibody which were not immobilized to the particles 101 were removed as below.

The dispersion liquid of the gold particles containing the CueO, the antibody, and polyoxyethylene(20)sorbitan monolaurate was poured to four centrifuge tubes (PC tube 3.0 mL; available from Beckman Coulter, Inc.). Each centrifuge tube had the dispersion liquid at a volume of 3 milliliters.

Glycerol at a volume of 0.05 milliliters (>99.5%; available from Life Technologies Corp.) was submerged in the bottom of each dispersion liquid. The glycerol served as a cushion.

Each centrifuge tube was inserted into a rotor (TLA-100, available from Beckman Coulter, Inc) and fixed to a centrifuge system (Optima TL; available from Beckman Coulter, Inc). The four centrifuge tubes were centrifuged at 70,000 rpm at a temperature of 4 degrees Celsius for 20 minutes.

A supernatant was removed from each centrifuge tube to leave condensed gold particle dispersion liquids (approximately 0.01 milliliter×4).

A Tris-buffered HCl solution (pH:8.0, 0.1 mM, 3 milliliters) containing polyoxyethylene(20)sorbitan monolaurate was added to the condensed gold particle dispersion liquid (0.01 milliliter). Hereinafter, this procedure is referred to as "procedure A". Hereinafter, the resultant buffer solution is referred to as "T-buffer solution".

The gold particle dispersion added the T-buffer solution were poured to four centrifuge tubes (PC tube 3.0 mL; available from Beckman Coulter, Inc.). Each centrifuge tube had the dispersion liquid at a volume of 3 milliliters. Glycerol at a volume of 0.05 milliliters (>99.5%; available from Life Technologies Corp.) was submerged in the bottom of each dispersion liquid. The glycerol served as a cushion. Each centrifuge tube was inserted into a rotor (TLA-100, available from Beckman Coulter, Inc) and fixed to a centrifuge rotor (Optima TL; available from Beckman Coulter, Inc). The four centrifuge tubes were centrifuged at 70,000 rpm at a temperature of 4 degrees Celsius for 20 minutes. A supernatant was removed from each centrifuge tube to leave condensed gold particle dispersion liquids (approximately 0.01 milliliter×4). Hereinafter, this procedure is referred to as "procedure B".

The procedure A and the procedure B were repeated again.

The gold particle dispersion liquid thus condensed was collected from the four centrifuge tubes, and the T-buffer solution was added so that the volume was adjusted to 1.2 milliliters. The concentration of the CueO contained in the gold particle dispersion liquid thus obtained was measured by a SDS-PAGE technique. The result was 0.02 milligram/milliliter. The gold particle dispersion liquid thus obtained was stored at a temperature of 4 degrees Celsius.

(Preparation of an Acetic Acid Buffer Solution)

While a value of a pH was measured with use of a pH meter, sodium hydroxide was added to acetic acid so as to prepare a 1M acetic acid buffer solution with a pH of 3. The acetic acid buffer solution is diluted by 5% so as to prepare an acetic acid buffer solution (pH:3) with a concentration of 50 mM. Similarly, an 1M acetic acid solution with a pH of 6 was prepared. Furthermore, an acetic acid buffer solution (pH:6) with a concentration of 50 mM was prepared.

(Preparation of an ABTS Solution)

2,2'-Azinobis(3-ethylbenzothiazoline-6-sulfonic Acid Ammonium Salt) (549 milligram, available from Tokyo Chemical Industry Co., Ltd., hereinafter referred to as "ABTS") was dissolved with ultrapure water to prepare an ABTS solution (100 mM) with a volume of 10 milliliter. ABTS served as an oxidation-reduction indicator.

The liquids shown in the following Table 1 were mixed to prepare an ABTS acetic acid buffer solution (pH:3) with a acetic buffer solution concentration of 1.0 mM. Similarly, An ABTS acetic acid buffer solution (pH:6) with a acetic buffer solution concentration of 1.0 mM was prepared.

TABLE 1

| liquid | Amount |
| --- | --- |
| Acetic buffer solution (pH: 3) with a concentration of 50 mM | 1 milliliter |
| ABTS solution | 0.05 milliliters |
| Ultrapure water | 47.95 milliliters |

The liquids shown in the following Table 2 were mixed to prepare an ABTS acetic acid buffer solution (pH:3) with a acetic buffer solution concentration of 0.5 mM. Similarly, An ABTS acetic acid buffer solution (pH:6) with a acetic buffer solution concentration of 0.5 mM was prepared.

TABLE 2

| liquid | Amount |
| --- | --- |
| Acetic buffer solution (pH: 3) with a concentration of 50 mM | 0.5 milliliter |
| ABTS solution | 0.05 milliliters |
| Ultrapure water | 48.45 milliliters |

The liquids shown in the following Table 3 were mixed to prepare an ABTS acetic acid buffer solution (pH:3) with a acetic buffer solution concentration of 5 mM. Similarly, An ABTS acetic acid buffer solution (pH:6) with a acetic buffer solution concentration of 5 mM was prepared.

TABLE 3

| Liquid | Amount |
| --- | --- |
| Acetic buffer solution (pH: 3) with a concentration of 50 mM | 5 milliliter |

TABLE 3-continued

| Liquid | Amount |
|---|---|
| ABTS solution | 0.05 milliliters |
| Ultrapure water | 43.95 milliliters |

The liquids shown in the following Table 4 were mixed to prepare an ABTS acetic acid buffer solution (pH:3) with a acetic buffer solution concentration of 10 mM. Similarly, An ABTS acetic acid buffer solution (pH:6) with a acetic buffer solution concentration of 10 mM was prepared.

TABLE 4

| Liquid | Amount |
|---|---|
| Acetic buffer solution (pH: 3) with a concentration of 50 mM | 10 milliliter |
| ABTS solution | 0.05 milliliters |
| Ultrapure water | 38.95 milliliters |

While a pH was measured with a pH meter, the ABTS acetic acid buffer solution (pH:3) with a acetic acid buffer solution concentration of 1.0 mM was added to the ABTS acetic acid buffer solution (pH:6) with a acetic acid buffer solution concentration of 1.0 mM so as to prepare an ABTS acetic acid buffer solution (pH:5.5) with a acetic acid buffer solution concentration of 1.0 mM. Similarly, an ABTS acetic acid buffer solution (pH:4.5) with a acetic acid buffer solution concentration of 1.0 mM was prepared.

Similarly, ABTS acetic acid buffer solutions (pH:5.5) each having a concentration 0.5 mM, 5 mM, and 10 mM were prepared. Furthermore, ABTS acetic acid buffer solutions (pH:4.5) each having a concentration 0.5 mM, 5 mM, and 10 mM were prepared.

Measurement of the Activity of CueO by an Absorbance Measurement Technique

The activity of the CueO was measured by an absorbance measurement technique with use of the oxidant-reduction indicator. For the absorbance measurement, an ultraviolet-visible spectrophotometer (UV-1600PC, available from Shimadzu Corp.) was used. As a measurement vessel, a cell (Disposable cell semi-micro, available from Kartell spa) having a light path length of 1 centimeter was used.

Measurement of a Blank Value

First, a blank value was measured as below. In the measurement of the blank value, an antigen was not used.

Figure 4:
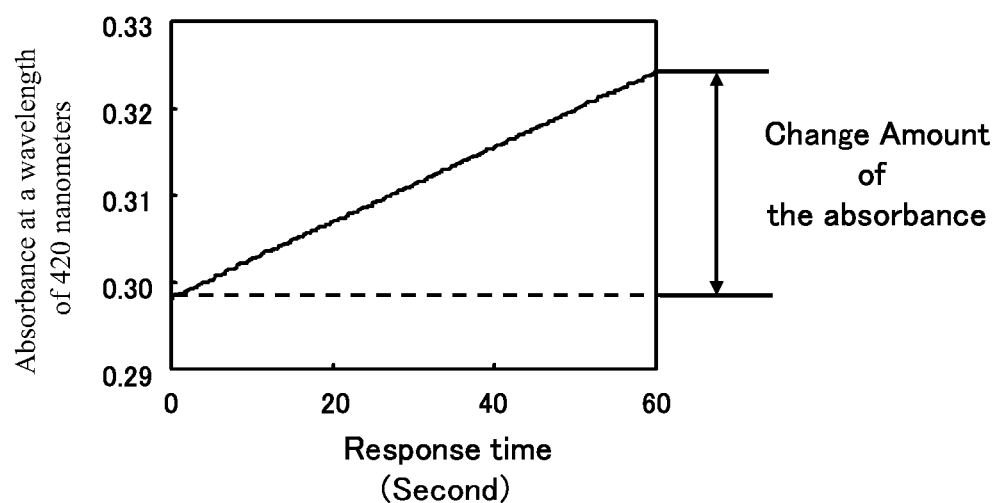
FIG. 4 shows the result of the absorbance measurement conducted in the example 1.

After the ABTS acetic acid buffer solution (1.0 mM; pH:4.5, 0.98 milliliter) was added to a cell, the cell was set in a visible-ultraviolet spectrophotometer. Next, the gold particle dispersion liquid (0.02 milliliter) was added to the cell. The absorbance of the ABTS acetic acid buffer solution was measured continuously (interval: 0.1 second) at a wavelength of 420 nanometers for sixty seconds. FIG. 4 shows the measurement result.

From the change amount of the absorbance measured for sixty seconds, the activity degree of the CueO was calculated on the basis of the following mathematical formula. About the unit of the activity degree of the CueO, 1 U means that the amount of the ABTS oxidized for sixty seconds is equal to 1 micromole. The result of the CueO activity measurement is shown in Table 5, which is described later.

$$\text{Activity of CueO(U/mg)} = A/\epsilon l B$$

where

A represents an absorbance (nanometer), $\epsilon$ represents a molar absoption coefficient of the ABTS at a wavelength of 420 nanometers, which was 36,000 (M$^{-1}$ cm$^{-1}$) in the present example, l represents a light path length, which was 1 centimeter in the present example, and B represents the concentration of the CueO, which was 0.02 milligram/milliliter in the present example.

In this manner, the blank value was measured.

Preparation of an Antigen-Antibody Mixture

After silica beads coated with BSA (diameter: 300 nanometers; 25 milligram/milliliter; available from micromod Partikeltechnologie GmbH) was added to the gold particle dispersion liquid (0.6 milliliter) as an antigen, the gold particle dispersion liquid was incubated at a temperature of 23 degrees Celsius and for thirty minutes. The gold particles each capturing the antigen was precipitated by centrifugation (2500 rpm, 23 degrees Celsius, 3 minutes), and the supernatant was removed. The T-buffer solution (1 milliliter) was added to the precipitate thus obtained, and the T-buffer solution was suspended. The gold particles were precipitated again by centrifugation (2500 rpm, 23 degrees Celsius, 3 minutes). The T-buffer solution (1 milliliter) was added to the obtained precipitate, and the T-buffer solution was suspended. The gold particles were precipitate again by centrifugation (2500 rpm, 23 degrees Celsius, 3 minutes). The T-buffer solution (0.6 milliliter) was added to the obtained precipitate, and the T-buffer solution was suspended. Thus, an antigen-antibody mixture was prepared.

Preparation of the Reaction Solution and Measurement of the Absorbance

After the ABTS acetic acid buffer solution (1.0 mM; pH:4.5, 0.98 milliliter) was added to a cell, the cell was set in a visible-ultraviolet spectrophotometer. Next, the gold particle dispersion liquid (0.02 milliliters) was added to the cell. The absorbance of the ABTS acetic acid buffer solution was measured continuously (interval: 0.1 second) at a wavelength of 420 nanometers for sixty seconds. From the measurement result, the activity of the CueO was calculated as a measurement value. The measurement value thus calculated was shown in the following Table 5, which is described later.

An amplification ratio was defined in the following equation:

(The amplification ratio)=(the measurement value)/
(the blank value).

Amplification ratios were calculated as described above using the ABTS acetic acid buffer solutions (pH:4.5, 5.0, and 5.5) each having an acetic acid buffer solution concentration of 1.0 mM and the ABTS acetic acid buffer solutions (pH:4.5, 5.0, and 5.5) each having an acetic acid buffer solution concentration of 10 mM. These results are shown in Table 1.

TABLE 5

| | pH | | | | | | | |
|---|---|---|---|---|---|---|---|---|
| | 4.5 | | | | 5.5 | | | |
| Acetic acid buffer solution concentration (mM) | 0.5 | 1 | 5 | 10 | 0.5 | 1 | 5 | 10 |
| Blank value[A] (U/mg) | 1.9 | 2.0 | 1.9 | 1.9 | 0.32 | 0.34 | 0.31 | 0.29 |
| Measurement Value[B] (U/mg) | 2.7 | 2.8 | 1.9 | 1.9 | 0.55 | 0.57 | 0.34 | 0.32 |
| Amplification ratio[B/A] | 1.4 | 1.4 | 1.0 | 1.0 | 1.7 | 1.7 | 1.1 | 1.1 |

As is clear from Table 5, when the concentration of the acetic acid buffer solution (more exactly, the concentration of the acetic acid contained in the ABTS acetic acid buffer solution) is 1.0 mM or less, the amplification ratio is 1.4 or more. On the contrary, the concentration of the acetic acid buffer solution is 5 mM or more, the amplification ratio is 1.1 at most.

Accordingly, a skilled person would understand from Table 5 that the antigen is detected if the amplification ratio is 1.4 or more. Furthermore, a skilled person would understand easily that the labeled-antibody 111 is not used in the present invention.

The present invention is used for a biosensor. The present invention is very useful for quick immunodiagnosis with multiplex assay.

[Referential Signs List]

| | |
|---|---|
| 101: | particle |
| 102: | multi-copper oxidase CueO |
| 103: | antibody |
| 104: | antigen |
| 105: | substrate |
| 106: | product |
| 107: | support |
| 108: | antibody |
| 109: | antigen |
| 110: | enzyme |
| 111: | labeled-antibody |
| 112: | substrate |
| 113: | product |

The invention claimed is:

1. A method for detecting an antigen, the method comprises steps of:
   (a) immersing particles in a first buffer solution which is predicted to contain the antigen; wherein
   an antibody and a multi-copper oxidase CueO are immobilized on each surface of the particles, and
   the antibody reacts specifically with the antigen;
   (b) recovering the particles obtained in the step (a);
   (c) mixing the particles recovered in the step (b) with 2,2'-Azinobis(3-ethylbenzothiazoline-6-sulfonic Acid (ABIS), and a second buffer solution so as to prepare a reaction solution; wherein:
   the second buffer solution contains a substrate of the multi-copper oxidase CueO,
   the second buffer solution has a pH of not less than 4.5 and not more than 5.5, and
   the second buffer solution has an ion strength falling within the range of not less than 0.3 mM and not more than 1.0 mM;
   (d) measuring an activity degree of the multi-copper oxidase CueO contained in the reaction solution obtained in the step (c) by an absorbance measurement technique; and
   (e) determining that the first buffer solution contains the antigen if the following formula is satisfied:
   the activity degree measured in the step (d) $\geqq 1.4 \times$(blank value) wherein the blank value represents the activity degree of the multi-copper oxidase CueO measured by an absorbance measurement technique in which the antigen is not used, however, the particles and the second buffer solution are used.

2. The method according to claim 1, wherein the particles are made of gold.

3. The method according to claim 1, wherein the first buffer solution is a Tris-buffered HCl solution, a Tris-buffered saline, or a phosphate buffer saline.

4. The method according to claim 1, wherein the second buffer solution contains oxygen and proton.

5. The method according to claim 1, wherein the second buffer solution is an acetic acid buffer solution, a citrate buffer solution, a succinic acid buffer solution, a phthalic acid buffer solution, or a 2-morpholinoethanesulfonic acid buffer solution.

* * * * *